(12) United States Patent
Tao et al.

(10) Patent No.: US 6,361,771 B1
(45) Date of Patent: Mar. 26, 2002

(54) ARPE-19 AS A PLATFORM CELL LINE FOR ENCAPSULATED CELL-BASED DELIVERY

(75) Inventors: Weng Tao, Lincon, RI (US); David H. Rein, Cambridge, MA (US); Brenda J. Dean, Cumberland, RI (US); Paul F. Stabila, Coventry, RI (US); Moses B.I. Goddard, Tiverton, RI (US)

(73) Assignee: Neurotech S.A., Evry (FR)

( * ) Notice: Subject to any disclaimer, the term of this patent is extended or adjusted under 35 U.S.C. 154(b) by 0 days.

(21) Appl. No.: 09/543,119

(22) Filed: Apr. 5, 2000

Related U.S. Application Data

(60) Provisional application No. 60/127,926, filed on Apr. 6, 1999.

(51) Int. Cl.[7] ............ A61K 48/00; A61K 9/22; C12N 15/163; C12N 5/108; A61M 3/00
(52) U.S. Cl. ............ 424/93.21; 435/320.1; 435/325; 435/455; 435/366; 435/371; 604/890.1; 604/43; 604/93
(58) Field of Search ............ 424/93.21, 93.2, 424/93.1; 514/44; 435/325, 455, 320.1, 366, 371; 604/890.1, 44, 93, 27, 174, 175

(56) References Cited

U.S. PATENT DOCUMENTS

| | | | |
|---|---|---|---|
| 4,892,538 A | 1/1990 | Aebischer et al. | 604/891.1 |
| 4,968,733 A | 11/1990 | Müller et al. | 521/64 |
| 4,976,859 A | 12/1990 | Wechs | 210/500.23 |
| 5,106,627 A | 4/1992 | Aebischer et al. | 424/424 |
| 5,156,844 A | 10/1992 | Aebischer et al. | 424/424 |
| 5,158,881 A | 10/1992 | Aebischer et al. | 435/182 |
| 5,283,187 A | 2/1994 | Aebischer et al. | 435/185 |
| 5,284,761 A | 2/1994 | Aebischer et al. | 435/182 |
| 5,512,600 A | 4/1996 | Mikos et al. | 521/61 |
| 5,550,050 A | 8/1996 | Holland et al. | 435/240.2 |
| 5,554,148 A | 9/1996 | Aebischer et al. | 604/890 |
| 5,614,404 A | 3/1997 | Mazzara et al. | 435/236 |
| 5,639,275 A | 6/1997 | Baetge et al. | 604/891 |
| 5,641,750 A * | 6/1997 | Louis | 514/12 |
| 5,653,687 A | 8/1997 | Mills et al. | 604/57 |
| 5,653,975 A | 8/1997 | Baetge et al. | 424/93.1 |
| 5,904,144 A * | 5/1999 | Hammang et al. | 128/898 |
| 6,020,192 A * | 2/2000 | Muzyczka et al. | 435/320.1 |

FOREIGN PATENT DOCUMENTS

| | | |
|---|---|---|
| WO | WO 92/19195 | 11/1992 |
| WO | WO 93/06222 | 4/1993 |
| WO | WO 94/01139 | 1/1994 |
| WO | WO 95/05452 | 2/1995 |
| WO | WO 97/34586 | 9/1997 |
| WO | WO 97/44065 | 11/1997 |
| WO | WO 98/05304 | 2/1998 |
| WO | WO 99/52573 | 10/1999 |

OTHER PUBLICATIONS

Wivel, N.A. & Wilson, J. M. Hematol. Oncol. Clin. North Am. 12:483–501, 1998.*
Dunn et al. Exp. Eye Res. 62:155–169, 1996.*
Aebischer et al. Nat. Med. 2:696–699, 1996.*
Cayouette et al. J. Neurosci. 18:9282–9293, 1998.*
American Type Culture Collection Web page <http://ph-age.atcc.org> (ATCC No. CRL–2302).
Dunn et al., 39 Invest. Ophthalmol. Vis Sci. 2744–9 (1998).
Emerich et al., 16 J. Neurosci. 5168–81 (1996).
Finnemann et al., 94 Proc. Natl. Acad. Sci. USA 12932–7 (1997).
Handa et al., 66 Exp. Eye. 411–9 (1998).
Holtkamp et al., 112 Clin. Exp. Immunol. 34–43 (1998).
Maidji et al., 70 J. Virol. 8402–10 (1996).

* cited by examiner

*Primary Examiner*—Dave T. Nguyen
*Assistant Examiner*—Quang Nguyen
(74) *Attorney, Agent, or Firm*—Mintz, Levin, Cohn, Ferris, Glovsky and Popeo, PC; Ivor R. Elrifi, Esq.; Christina V. Karnakis, Esq.

(57) ABSTRACT

ARPE-19 cells were evaluated as a platform cell line for encapsulated and un-encapsulated cell-based delivery technology. ARPE-19 cells were found to be hardy (the cell line is viable under stringent conditions, such as in central nervous system or intra-ocular environment); can be genetically modified to secrete the protein of choice; has a long life span; is of human origin; has good in vivo device viability; delivers efficacious quantity of growth factor; triggers no or low level host immune reaction, and is non-tumorigenic.

14 Claims, 2 Drawing Sheets

ARPE-19 AS A PLATFORM CELL LINE FOR ENCAPSULATED CELL-BASED DELIVERY

CLAIM OF PRIORITY

This application claims priority to U.S. provisional patent application No. 60/127,926, filed Apr. 6, 1999.

TECHNICAL FIELD OF THE INVENTION

This invention relates generally to cellular therapy and encapsulated devices.

BACKGROUND OF THE INVENTION

Growth factors have tremendous therapeutic potential for neurodegenerative disorders. However, growth factors have yet to be successfully developed into clinical treatments due to the fact that large proteins, like growth factors, do not cross the blood-brain barrier. The transplantation of cells genetically engineered to produce growth factors offers a partial solution to the problem of growth factor delivery, because grafts of growth factor-producing cells can bypass the blood-brain barrier and deliver the therapeutic factors directly to the target site. Unfortunately, these transplants are subject to host immune rejection and require immunosuppression. Also, grafts of some genetically engineered cell lines can form lethal tumors.

Implanting cells that have been macroencapsulated in semi-permeable polymer membranes provides a better solution to these problems. Mammalian cells that have been genetically engineered to produce growth factors can be encapsulated in semipermeable polymer membranes. The semipermeable membranes protect the encapsulated cells from acute host immune rejection, but allow the delivery of the therapeutic agents into the host tissue. These small bioartificial devices (cells macroencapsulated in semipermeable membranes) can be implanted directly into the target site for site-specific, continuous, long-term, low-level delivery of the desired factors. Encapsulating cells in semipermeable membranes also reduces the risk of tumor development. Furthermore, polymer-encapsulated cell transplants have lower incidences of infection, because the transplants require only a single penetration into the target site for continuous growth factor delivery.

Regarding the delivery of desired growth factors, preclinical studies have shown that polymer-encapsulated cells can deliver ciliary neurotrophic factor (CNTF) continuously with therapeutic efficacy in rodent models (Emerich et al., 16 J. Neurosci. 5168–81 (1996)). Clinical trials support the safety of chronic CNTF delivery into the human central nervous system (CNS) with polymer-encapsulated cells (Aebischer et al., 7 Hum. Gene Ther. 851–60 (1996), Aebischer et al., 2 Nature Medicine 696–9 (1996)). However, a major challenge in translating such successes from rodent models to humans is ensuring long-term cell viability in encapsulated devices in vivo.

SUMMARY OF THE INVENTION

The ARPE-19 cell line is a superior platform cell line for encapsulated cell based delivery technology and is also useful for unencapsulated cell based delivery technology. The ARPE-19 cell line is hardy (i.e., the cell line is viable under stringent conditions, such as implantation in the central nervous system or the intra-ocular environment). ARPE-19 cells can be genetically modified to secrete a substance of therapeutic interest. ARPE-19 cells have a relatively long life span. ARPE-19 cells are of human origin. Furthermore, encapsulated ARPE-19 cells have good in vivo device viability. ARPE-19 cells can deliver an efficacious quantity of growth factor. ARPE-19 cells elicit a negligible host immune reaction. Moreover, ARPE-19 cells are non-tumorigenic.

The therapeutic usefulness of polymer-encapsulated ARPE-19 cell-based delivery of ciliary neurotrophic factor (CNTF) for treatment of degenerative diseases was shown in both a rodent and canine model of retinitis pigmentosa. ARPE-19 cells were genetically modified to secrete CNTF. Encapsulated genetically modified ARPE-19 cells delivered a consistent amount of CNTF, for example, over a 7-week implantation interval. Cell viability within the encapsulated devices was excellent. The presence of the encapsulated cell device in the eye caused no significant adverse effects on the retina. These results provide a proof of principle for the therapeutic potential of encapsulated ARPE-19 cell-based delivery of desired neurotrophic factors.

DETAILED DESCRIPTION OF THE INVENTION

Figure 1:
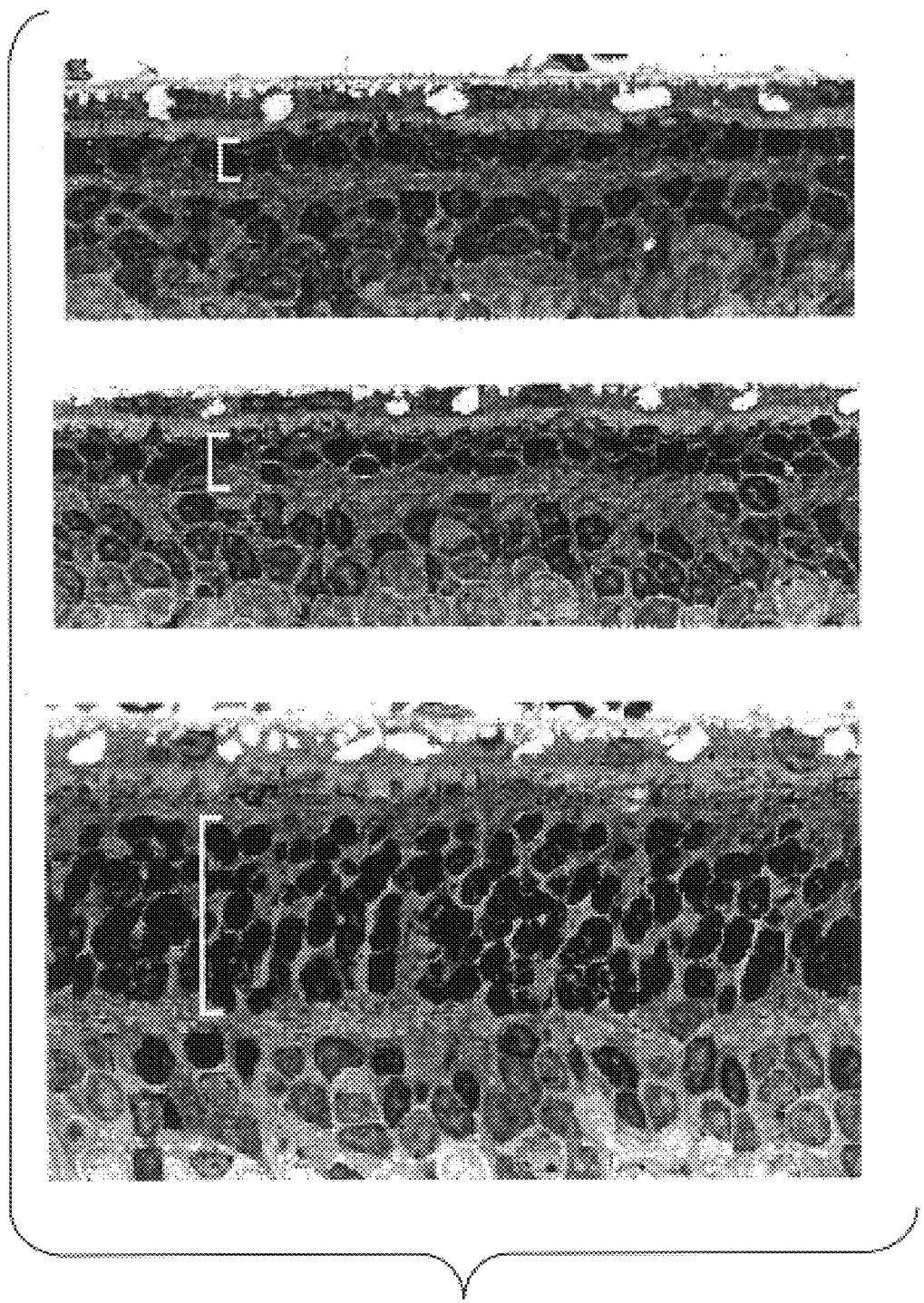
FIG. 1 is a photograph showing protection of photoreceptors in transgenic rats carrying the rhodopsin mutation S334ter by ARPE-19/CNTF cells. (A) S334ter untreated rat; (B) ARPE-19 parental cell treated control rat; and (C) ARPE-19/CNTF cell treated rat.

A. ARPE-19 Cell Line as a Platform Cell Line for an Encapsulated Cell Based Delivery System To be a platform cell line for an encapsulated cell based delivery system, the cell line should have as many of the following characteristics as possible: (1) The cells should be hardy under stringent conditions (the encapsulated cells should be functional in the avascular tissue cavities such as in the central nervous system or the eye, especially in the intra-ocular environment). (2) The cells should be able to be genetically modified (the desired therapeutic factors needed to be engineered into the cells). (3) The cells should have a relatively long life span (the cells should produce sufficient progenies to be banked, characterized, engineered, safety tested and clinical lot manufactured). (4) The cells should preferably be of human origin (which increases compatibility between the encapsulated cells and the host). (5) The cells should exhibit greater than 80% viability for a period of more than one month in vivo in device (which ensures long-term delivery). (6) The encapsulated cells should deliver an efficacious quantity of a useful biological product (which ensures effectiveness of the treatment). (7) The cells should have a low level of host immune reaction (which ensures the longevity of the graft). (8) The cells should be nontumorigenic (to provide added safety to the host, in case of device leakage).

We screened and characterized several cell lines, identified optimal encapsulated cell device configurations, and evaluated cell viabilities within devices in different animal models. We found that the ARPE-19 cell line (Dunn et al., 62 Exp. Eye Res. 155–69 (1996), Dunn et al., 39 Invest. Ophthalmol. Vis. Sci. 2744–9 (1998), Finnemann et al., 94 Proc. Natl. Acad. Sci. USA 12932–7 (1997), Handa et al., 66 Exp. Eye. 411–9 (1998), Holtkamp et al., 112 Clin. Exp. Immunol. 34–43 (1998), Maidji et al., 70 J. Virol. 8402–10 (1996)) had all of the characteristics of a successful platform cell for an encapsulated cell-based delivery system. The ARPE-19 cell line was superior to the other cell lines that we tested.

The ARPE-19 cell line is available from the American Type Culture Collection (ATCC Number CRL-2302). ARPE-19 cells are normal retinal pigmented epithelial (RPE) cells and express the retinal pigmentary epithelial cell-specific markers CRALBP and RPE-65. ARPE-19 cells form stable monolayers, which exhibit morphological and functional polarity.

ARPE-19 cells are cultured in Complete Growth Medium, the serum-containing medium recommended by the cell depositor. Complete Growth Medium is either a 1:1 mixture of Dulbecco's modified Eagle's medium and Ham's F12 medium with 3 mM L-glutamine, 90%; fetal bovine serum, 10% or a 1:1 mixture of Dulbecco's modified Eagle's medium and Ham's F12 medium with HEPES buffer containing 10% fetal bovine serum, 56 mM final concentration sodium bicarbonate and 2 mM L-glutamine and incubated at 37° C. in 5% $CO_2$. The cells were plated. The cells were typically grown in Falcon tissue culture treated 6 or 12-well plates or T25 or T75 flasks.

For subculturing, spent medium is removed, and the ARPE-19 cells are rinsed with 0.05% trypsin, 0.02% EDTA solution, and the trypsin is removed. One to two ml of additional trypsin solution is added. The culture is incubated at room temperature (or at 37° C.) until the ARPE-19 cells detach. A subcultivation ratio of 1:3 to 1:5 is recommended.

1. The ARPE-19 cell line is hardy.

To evaluate the hardiness of cell lines, a three-step screen was established. (a) Cell viability screen (The cells were evaluated under stressed conditions using artificial aqueous humor (aAH) medium or artificial cerebral spinal fluid (aCSF) medium). (b) In vitro ECM screen (The cells were evaluated in an in vitro extra-cellular matrix (ECM) screen). (c) In vivo device viability screen (The encapsulated cells were evaluated in an in vivo membrane screen).

(a) Cell viability in vitro screen. Effect of aAH and aCSF on test cells (including ARPE-19 cells) was examined. Artificial aqueous humor (aAH) and artificial cerebral spinal fluid (aCSF) were formulated according to the protocols from Geigy Scientific Tables. The detailed formulations are listed in TABLE 1:

TABLE 1

FORMULATIONS FOR AAH & ACSF

| | Artificial Aqueous Humor (aAH) | | Artificial Cerebral Spinal Fluid (aCSF) | |
|---|---|---|---|---|
| | | (mg/L) | | (mg/L) |
| Amino Acids | ($\mu$M) | | ($\mu$M) | |
| L-Alanine | 294 | 26.19 | 28 | 2.4945 |
| L-α-Amino butyric acid | 31.4 | 3.24 | | |
| L-Arginine.HCl | 133 | 28.02 | 19 | 4.0033 |
| L-Asparagine | 49.2 | 6.49 | 6.3 | 0.9456 |
| L-Aspartic acid | 1 | 0.13 | 0.45 | 0.0599 |
| L-Citrulline | 9.8 | 1.72 | | |
| L-Cystine.2HCl | | | 0.1 | 0.0313 |
| Ethanolamine | | | 16.7 | 1.02 |
| L-Glutamic acid | 12 | 1.77 | 11.4 | 1.6769 |
| L-Glutamine | 717 | 104.75 | 515.7 | 75.3438 |
| Glycine | 16.7 | 1.25 | 6.2 | 0.4654 |
| L-Histadine.HCl.$H_2O$ | 77.9 | 16.33 | 12.6 | 2.6410 |
| L-Isoleucine | 79.8 | 10.47 | 4.6 | 0.6035 |
| L-Leucine | 192 | 25.19 | 12 | 1.5744 |
| L-Lysine.HCl | 155 | 28.30 | 24.9 | 4.5467 |
| L-Methionine | 44.4 | 6.62 | 2.7 | 0.4028 |
| L-Ornithine.HCl | 25.3 | 4.27 | 4.5 | 0.7587 |
| L-Phenylalanine | 119 | 19.66 | 7.8 | 0.2886 |
| O-Phosphorylethanolamine | | | 5.2 | 0.7337 |
| L-Proline | 16 | 1.84 | | |
| L-Serine | 179 | 18.81 | 25.4 | 2.6695 |
| Taurine | 39.1 | 4.89 | | |
| L-Threonine | 152 | 18.10 | 28.8 | 3.4301 |
| L-Tryptophan | 31.9 | 6.51 | 1.2 | 0.2450 |
| L-Tyrosine | 123 | 22.26 | 7.2 | 0.6214 |
| L-Valine | 388 | 45.43 | 17.3 | 2.0258 |
| Inorganic Salts | (mM) | | (mM) | |
| Sodium Bicarbonate | 21.6 | | 22.6 | 1898.626 |
| Sodium Chloride | 120 | | | |
| Potassium Chloride | 3.2 | | 4 | 298.2000 |
| Sodium Phosphate | 111 | | 0.25 | 34.5000 |
| Cupric Sulfate | 0.002 | | 0.00025 | 0.0624 |
| Copper | 0.0028 | | | |
| Zinc Sulfate | | 1.0 | 0.00064 | 0.1826 |
| NaF | | | 0.005 | 0.2100 |
| MnCl2 | | 0.1 | 0.000021 | 0.00415 |
| MgCl2 | | | 0.5 | 101.6500 |
| KI | | | 0.000016 | 0.002656 |
| KBr | | | 0.029 | 3.4510 |
| Short-Chain Fatty Acids | (mM) | | | |
| Urea | 4.51 | 270.87 | | |
| DL-Lactic acid | 4.69 | 422.48 | 1.47 mM | 132.4176 |
| Citric acid | 0.133 | 25.55 | 0.176 mM | 33.8096 |
| Pyruvic acid | | | 0.14 mM | 11.9762 |
| Acetic acid | | | 116 $\mu$M | 7.0830 |
| Propionic acid | | | 2.8 $\mu$M | 0.2074 |
| Isobutyric acid | | | 1.8 $\mu$M | 0.1586 |
| n-Butyric | | | 1.4 $\mu$M | 0.1234 |

TABLE 1-continued

FORMULATIONS FOR AAH & ACSF

| | Artificial Aqueous Humor (aAH) | | Artificial Cerebral Spinal Fluid (aCSF) | |
|---|---|---|---|---|
| | (mg/L) | | (mg/L) | |
| acid | | | | |
| Isovaleric acid | | | 1.35 μM | 0.1378 |
| α-Oxoglutaric acid | | | 8.9 μM | 1.3000 |
| Oxalacetic acid | | | 7.2 μM | 0.9511 |
| Succinic acid | | | 28.5 μM | 3.3659 |
| Ketone Bodies (as acetone) | | | 117 μM | 6.7954 |
| Acetoacetic acid | | | 26.2 μM | 2.6700 |
| DL-B-Hydroxybutyric acid | | | 46.4 μM | 5.5810 |
| Vitamins | | | | |
| Nicotinamide | 40 nmol/ eye | 2.44 | | |
| Trigonelline | 70 nmol/ eye | 6.08 | | |
| B12 | 22.1 pM | 0.0000299 | 13.58 pM | 1.8406E-05 |
| L-Ascorbic acid | 810 pM | 234.53 | 60 μM | 10.5660 |
| Nicotinic acid | | | 2.4 μM | 0.2954 |
| D-Pantothenic acid | | | 2.37 μM | 0.5648 |
| Thiamine (B1) | | | 15 nM | 0.0050595 |
| B6 (pyridoxine) | | | 2.2 nM | 0.00045232 |
| Folic acid | | | 62.55 nM | 0.02760957 |
| Biopterin | | | 4.3 nM | 0.00101996 |
| Lipids | | | | |
| Triglycerides | | | 4.17 mg/L | 4.1700 |
| Cholesterol | | | 4.63 mg/L | 4.6300 |
| Phospholipids | | | 5.49 mg/L | 5.4900 |
| Fatty acids | | | 7.36 mg/L | 7.3600 |
| Prostaglandin PGE1 | | | 1.31 nM | 0.0004644 |
| Prostaglandin PGF2a | | | 1.98 nM | 0.00094169 |
| Carbohydrates | | | | |
| D(+)-Glucose | 0.756 g/L | 756.84 | | |
| Total Protein | | | | |
| FBS | 10.6 ml/L | 450.00 | 8.4 ml/L | |
| Transferrin | 59 mg/L | 59.00 | | |

The cells were plated initially in serum containing medium to allow the cells to attach. The cells were plated at 60,000/cm$^2$, and incubated in a 37° C. incubator with 5% $CO_2$. After the cells had attached (18–24 hours), the growth medium was removed and the cells were washed 2× with Hank's balanced salt solution (HBSS) to remove serum. The medium was replaced with either aAH or aCSF (pre-warmed to 37° C.). Spent aAH or aCSF was replaced with fresh aAH or aCSF every other day (Monday, Wednesday, Friday schedule). The test cells were evaluated daily for morphology, viability and % confluency (compared to control) by microscopic examination. All cells were evaluated for a one-week duration. The observations were documented with photographs.

A control of each cell line in complete growth medium was carried throughout the screen for comparison with the experimental group. At the end of the test period, the results were recorded in number of cells and % confluency with a note about morphology. Also, viability staining such as fluorescein diacetate/propidium iodide (FDA-PI) was used to access viability of the culture. Cells that passed initial cell viability in vitro screen proceeded to the in vitro ECM screen.

(b) In vitro extra-cellular matrix (ECM) screen. Cell survival using various extra cellular matrices (ECM) was evaluated under aCSF and hypoxic conditions and the ECM that provided the best survival was selected. For each potential "Hardy Cell" candidate, the cell-substrate interaction was evaluated for the following extra-cellular matrices (TABLE 2):

TABLE 2

EXTRA CELLULAR MATRIX

| Type | Source |
|---|---|
| Primaria cultureware | synthetic |
| Collagen Type IV | human placenta |
| Cell-Tak | mussel |
| Fibronectin | human placenta |
| Poly-D-lysine | synthetic |
| Laminin | synthetic |
| Elastin | bovine |
| Tissue culture plastic | control |

The optimal ECM was used to coat the scaffold to which the cells will ultimately adhere inside the device. The optimal combination of "Hardy cell" candidate, ECM, and scaffold were encapsulated using a membrane with intermediate permeability and tested under stringent tissue culture conditions (aAH or aCSF). Survival was monitored at 1, 2 and 4-week intervals, using both metabolic and histologic methods.

(c) In vivo device viability screen: Hardy cells from the ECM screen were further evaluated using different membranes and scaffolds. The optimal combinations of cell/ECM/scaffold were encapsulated with different membrane types (membrane with different diffusive properties) and devices were implanted in the rat ventricle. Device performance was evaluated after a one month in vivo implantation duration.

ARPE-19 viability (as well as other desirable characteristics) was superior to other cell lines tested. TABLE 3 summarizes the results for human cell lines.

TABLE 3

CELL SCREENING RESULTS - HUMAN CELL LINES

| # | Cell Line | Tissue Origin | Morphology | Status In Screen |
|---|---|---|---|---|
| 1 | C3A* | Hepatoblastoma | Polygonal | Viability: passed |
| 2 | HepG2* | Hepatoblastoma | Polygonal | Viability: passed |
| 3 | HFCH | Fetal femur | Chondroblast | Viability: eliminated |
| 4 | Hs27** | Foreskin | Fibroblast | Viability: passed |
| 5 | Hs2-MX1 | Foreskin | Fibroblast | Viability: eliminated |
| 6 | HS683 | Glioma | Glioblast | Viability: eliminated |
| 7 | A172 | Glioblastoma | Glioblast | Viability: eliminated |

TABLE 3-continued

CELL SCREENING RESULTS - HUMAN CELL LINES

| # | Cell Line | Tissue Origin | Morph-ology | Status In Screen |
|---|---|---|---|---|
| 8 | HS578BST*** | Normal breast | Fibroblast | Viability: passed |
| 9 | 184B5 | Mammary | Epithelial | Viability: eliminated |
| 10 | HCN-1A | Cortical | Neuron | Viability: eliminated |
| 11 | HCN-2 | Cortical | Neuron | Viability: eliminated |
| 12 | HEPM | Palate | Fibroblast | Matrix: eliminated |
| 13 | NHLF | Lung | Fibroblast | Matrix: eliminated |
| 14 | HL60 | Leukemic | Monocyte | Viability: eliminated |
| 15 | Skin | Cri du Chat | Fibroblast | Viability: eliminated |
| 16 | 9.5 Fbr | Forebrain | Neural stem | Viability: eliminated |
| 17 | FHS 74 INT | Small intestine | Epithelial | Viability: eliminated |
| 18 | MRC-5 | Lung | Fibroblast | Viability: eliminated |
| 19 | MRC-9 | Fetal lung | Fibroblast | Viability: eliminated |
| 20 | WI-38 | Lung | Fibroblast | Viability: eliminated |
| 21 | T98G | Glioblastoma | Glioblast | Viability: eliminated |
| 22 | ARPE-19 | Retina | Epithelial | Viability: passed |

*These cell lines are tumorigenic
**This cell line requires immortalization
***This cell line has slow growth rate (double every 5 days)

Table 4 summarizes the results for xenogeneic cell lines.

TABLE 4

CELL SCREENING RESULTS - XENOGENEIC CELL LINES

| # | Cell Line | Tissue Origin | Morph-ology | Status In Screen |
|---|---|---|---|---|
| 1 | SC-1 | Rat nerve | Schwann | Viability: eliminated |
| 2 | SIRC* | Rabbit cornea | Fibroblast | Viability: passed |
| 3 | NCTC 4206 | Hamster peritoneum | Fibroblast | Viability: eliminated |
| 4 | Clone 9 | Rat liver | Epithelial | Viability: eliminated |
| 5 | TM4 | Rat Sertoli | Epithelial | Viability: eliminated |
| 6 | PAS | Pig embryo brain | Astrocyte | Viability: eliminated |
| 7 | BHK | Hamster kidney | Fibroblast | Viability: eliminated |
| 8 | CNTF clone 72 | | | Viability: eliminated |
| 9 | NT4/5 clone 45 | | | Viability: eliminated |
| 10 | CHO | Hamster ovary | Epithelial | In vivo: eliminated* |
| 11 | 3T3 | Mouse fibroblast | Fibroblast | In vivo: eliminated |
| 12 | C2Cl2 | Mouse myoblast | Myblast | Viability: eliminated |
| 13 | B14RAF28-G3 | Hamster peritoneum | Fibroblast | Viability: eliminated |
| 14 | BRL3A | Rat liver | Epithelial | Viability: eliminated |
| 15 | PC12 | Rat pheochrom. | Pheochrom. | Viability: eliminated |

*The cell line is xenogeneic-originated non-human

2. ARPE-19 cells can be genetically modified.

The ARPE-19 cells can be genetically modified to produce a desired factor. We transfected ARPE-19 cells with appropriate plasmids using Fugene 6 (a lipid-based transfection reagent from Boehringer Ingelheim) according to the manufacturer's protocol. Polyclonal stable cell lines were selected, for example, using G418 (Gibco-BRL, Gaithersburg, Md.) at a concentration of 1.0 mg/ml and maintained at 0.25 mg/ml. Stable ARPE-19/GDNF, ARPE-19/CNTF and ARPE-19/EGFP cell lines were established. GDNF or CNTF output, as measured by ELISA, was between 100–200 ng/million cells/24 hr(ng/M/d). (This is one example of a "therapeutically effective" amount.)

(a) CNTF. ARPE-19 cells were transfected with various CNTF-encoding plasmids (see, TABLE 5). ARPE-19 cells transfected with P544 (pNUT-IgSP-CNTF (genomic)) were designated NTC201 (ARPE/CNTF; ARPE-P444; CNCM Registry No: I-2524).

TABLE 5

CNTF TRANSFECTION

| IgSP-CNTF | PcDNA3.1. (hCMV)** | pPI (mPGK)** | pNUT (mMT-1)** |
|---|---|---|---|
| cDNA | P566* | P565* | — |
| Genomic | — | — | P544 |

*verified by restriction analysis only
**Promoters: hCMV, human cytomegalovirus: mPGK, mouse phosphoglycerate kinase; mMT-1, mouse metallothionine.

(b) GDNF. ARPE-19 cells were transfected with five plasmid constructs expressing hGDNF under different promoters and signal sequences (TABLE 6). Cells were transfected by FuGene 6. Transfected cells were selected by resistance to the drug G418 (Geneticin) or methotrexate.

TABLE 6

PLASMIDS EXPRESSING hGDNF UNDER DIFFERENT PROMOTERS AND SIGNAL SEQUENCES

| Plasmid | Vector | cDNA | Promoter | Signal Peptide | Selection Marker | Amplification Marker |
|---|---|---|---|---|---|---|
| p142 | pcDNA3 | hGDNF | CMV | HGDNF | neomycin | |
| p168 | pcDNA3 | hGDNF | CMV | Ig | neomycin | |
| p558 | pPI-DN | hGDNF | pgk | Ig | neomycin | DHFR |
| p559 | pPI-DN | hGDNF | pgk | HGDNF | neomycin | DHFR |
| p560 | pNUT | hGDNF | MT-1 | HGDNF | DHFR | DHFR |

CMV = cytomegalovirus; PGK = phoshoglycerate kinase; MT = metallothionein; Ig = immunoglobulin; hGDNF = human glial cell line derived neurotrophic factor; DHFR = dihydrofolate reductase Conditioned media from the transfected cells was collected and analyzed by Western Blot for the expression of hGDNF. GDNF is a heparin-binding, disulfide-bonded homodimer that is heterologously glycosylated and migrates on SDS-PAGE with an apparent molecular weight of 33–45 kDa. Unglycosylated GDNF has an apparent molecular weight of 30 kDa (Lin et al., 63(2) J. Neurochem. 758–768 (1994)). Conditioned media were collected from parental and transfected ARPE-19 for Western Blot analysis of hGDNF expression. GDNF was semi-purified from conditioned media by Cellufine, a cellulose affinity media (Amicon Matrex) with properties similar to heparin sepharose. Non-specifically bound proteins were washed away in 25 mM Hepes/150 mM NaCl pH 7.4 and bound proteins were eluted in 25 mM Hepes/2 M NaCl, pH 7.4. The eluted proteins were concentrated with Pall Filtron microfuge concentrators (MWCO 3 kDa) and buffer exchanged with 25 mM Hepes to achieve a 200-fold concentration of conditioned media (CM). Up to 1/20 of the non-reduced, semi-purified CM were loaded onto a denaturing 10–20% gradient Tricine SDS-PAGE gel and electroblotted onto Immobilon-P PVDF membranes. Western Blots were detected by chemiluminescence.

A panel of 5 antibodies (3 polyclonals and 2 monoclonals) were used to detect GDNF production. Chemicon rabbit pAB (AB1454); Promega chicken pAb (G2791); R&D Systems goat pAb (AF212NA); Promega mAb (available only in GDNF E, ImmunoAssay Systems G3240/G3520 kit); R&D Systems mAb (MAB212). The antibodies with the least non-specific binding and highest sensitivity were monoconals from Promega and R&D Systems. NTC200p559 (ARPE/GDNF; ARPE-19/p559; CNCM Registry No: I-2523).

(c) Green fluorescent protein. ARPE-19 cells were transfected with the Green Fluorescent Protein (GFP) encoding plasmid pEGFP-N1 (Clontech, Palo Alto, Calif.). Since expression of Green Fluorescent Protein can be easily monitored visually using a fluorescent microscope, the stability of the heterologous expression of this foreign gene can be monitored throughout many generations. Briefly, ARPE-19 cells were genetically modified to express Green Fluorescent Protein. Clonal lines were derived from a polyclonal ARPE-19/GFP by limiting dilution, then expanded to a T-25 flask. One of these lines, NTC200p393(1) (ARPE/GFP; P-393-1; CNCM Registry No: I-2522) was maintained and passed weekly.

P393-1 was passed at least 5 times since having been expanded to the initial T-25. P393-1 had undergone over 30 doublings since being cloned. Green Fluorescent Protein expression continued to be robust throughout the lines entire lifespan.

3. ARPF-19 has a long life span.

The growth rate of ARPE-19 cells in serum culture medium (DMEM/F12+10% FBS) is approximately 1 doubling/48 hr. The total passage number exceeded 100. The ARPE-19 cells appear to have a normal phenotype and grow at a stable rate.

4. ARPE-19 is of human origin.

ARPE-19 is a spontaneously arising retinal pigment epithelia (RPE) cell line derived in 1986 from the normal eyes of a 19-year-old human male who died from head trauma in a motor vehicle accident (ATCC).

5. ARPE-19 exhibits acceptable in vivo device viability.

The device viability of encapsulated ARPE-19 cells was evaluated in vivo in the central nervous system and eye environments. ARPE-19 cells or ARPE-P544 cells (expressing CNTF) were encapsulated and the resulting devices were implanted into rat ventricle (ICV), rabbit eye, dog eye, and sheep intrathecal space. Briefly, the cells were encapsulated with either CytoPES 14 (polyethersulfone) or CytoPES 1000 membranes. For CytoPES14 membranes, the matrix scaffold was PET yarn, 6 strands; the extra-cellular matrix (ECM) coating was Laminin/Collagen IV; the device anchor was a titanium loop; the total device length was 1.1 cm; the cell load density was 66 K/$\mu$l, the load volume was 6 $\mu$l, the holding media was Ultra Culture. For CytoPES 1000 membranes, the matrix was PET yarn coated in a two step coating process with human collagen type IV and laminin at 1 mg/ml and 0.1 mg/ml respectively. For rat ICV, the devices were 0.7 cm in length. For dog and rabbit eye, the devices were 1.0 cm in length. For sheep intrathecal space, the devices were 7.0 cm in length. All devices were non-strutted and E-Beam (electron-beam) sterilized at Titan Systems (Denver, Colo.). The hold media were Ultraculture+1% L-Glutamine or ACSF+0.83% FBS, 0.26% L-Glutamine and buffer with 15 mM HEPES.

One month after surgical implantation, the devices were explanted and cell viability in the devices was evaluated histologically. The cell device viability was excellent in all implantation sites examined. The results are presented in TABLE 7.

TABLE 7

ARPE-P544 CELL DEVICE VIABILITY AFTER 1 MONTH IN VIVO

| Animal model | Device Design | Implantation site | Device viability |
|---|---|---|---|
| Rat | 0.7 cm in length | ICV | Viable |
| Rabbit | 1.0 cm in length | Intra-vitreous | Viable |
| Dog | 1.0 cm in length | Intra-vitreous | Viable |
| Sheep | 7.0 cm in length | Intrathecal | Viable |

6. ARPE-19 can be modified to deliver an efficacious quantity of growth factor: Proof of concept.

The therapeutic effect (retinal protection) of CNTF secreting ARPE-P544 cells was evaluated in both rat and dog animal models for retinal degeneration.

(a) Transgenic rat test—unencapsulated ARPE-544. At postnatal day (PD) 9, approximately $10^5$ ARPE-P544 cells in 2 $\mu$l phosphate buffered saline (PBS) were injected into the vitreous of the left eye of S334ter-3 rats using 32 gauge needles. Control eyes (right eyes) were injected with un-transfected ARPE-19 cells. For the CNTF bolus injections, 1 $\mu$g CNTF in 1 $\mu$l of PBS was injected into the vitreous at PD 9. The eyes were collected at PD 20, and processed for histologic evaluation. Plastic embedded sections of 1 $\mu$m thickness were examined by light microscopy.

In the untreated S334ter transgenic rats, severe photoreceptor degeneration was observed by post delivery (PD) day 20. The outer nuclei layer (ONL) had only one row of nuclei. In the ARPE-P544 injected eyes, the ONL had 5–6 rows of nuclei, while in the control eyes injected with ARPE-19 cells, there were 1–2 rows of nuclei remaining. In animals treated with a bolus injection of purified human recombinant CNTF, the ONL had 2–3 rows of nuclei. The results are presented in FIG. 1.

A sustained release of CNTF from the unencapsulated ARPE-19 cells transfected with CNTF achieved better protection of photoreceptors than a bolus injection of purified CNTF protein.

(b) Mutant dog test—encapsulated ARPE-544. This study was conducted in rod-cone dysplasia (rcd 1) dogs with the rod cyclic GMP phosphodiesterase beta subunit gene (PDE6B) mutation. One set of tests used 6 dogs at 7 weeks of age. Two dogs were affected (retinal degeneration) and 4 were gene carriers (normal). For the two affected dogs, the left eye received an ARPE-P544 containing device and the right eye was untreated (control). For the 4 normal dogs, both eyes received ARPE-P544 containing devices. The devices were 1.1 cm in length including a titanium anchoring loop. Each device consisted of the CytoPES14 membrane and a PET yarn scaffold coated with laminin and collagen type IV. The duration of the study was 7 weeks. All devices except two in one normal dog were explanted and evaluated for CNTF output by ELISA (R&D Systems) and for cell viability by histological analysis.

The CNTF output for ARPE-P544 was estimated at 150–200 ng/$10^6$ cells/24 hr (un-encapsulated, in vitro, in complete growth media). The cells were grown in T-75 flasks and maintained in a DMEM-based medium supplemented with 10% FBS, in a 5% $CO_2$, 95% humidity, 37° C. incubator. Prior to encapsulation, the CNTF output of the cells was assayed by an enzyme linked immunosorbent assay (ELISA).

Prior to encapsulation, the devices were assembled in a controlled environment, packaged and then e-beam sterilized (see below for details of other encapsulation protocols). The ARPE-19 cells were harvested on the day of encapsulation, and suspended in Ultraculture serum-free media at a density of 66,000 cells/$\mu$l. The sterile devices were then loaded using a Hamilton syringe with a volume of 6 µl each. After the infusion of the cellular suspension, the final seal was applied. The cell-loaded devices were maintained in Ultraculture supplemented with 1% L-glutamine. After 7 days, all devices were assayed for CNTF output by ELISA. In vitro cohorts of devices were maintained in six well plates throughout the course of study. Feeding was performed once a week.

For surgery, animal was sedated with ketamine and xylazine. Body weight and temperature were measured and pupils were dilated with two drops each of Mydfrin (2.5%) and Cyclogyl (1%). Blood samples were drawn and an intravenous (IV) line established. Anesthesia was induced with sodium pentothal. The animal was then endotracheally intubated and moved into the operating room where inhalation of isoflurane was established, and vital signs monitored. Alternatively, inhalation of isoflurane was established before intubation, obviating the need for sedatives and pentothal induction. The animal was then positioned on the operating table in the lateral decubitus position and covered with a heating pad.

In the eye implantation procedure, the lids and periorbital area of the eyes were scrub-prepped with dilute iodophor solution, and sterile drapes were secured. The eyelids were retracted with a lid speculum and the eye positioned with a single conjunctival stitch placed at the limbus and clamped to the drapes, rotating the eye medially. Under microscopic visualization, a 6 mm incision was made through both conjunctiva and tenons approximately 3.5 mm from the limbus using a blunt scissors. Using a #75 blade a 2.0–3.0 mm longitudinal incision was made through the sclera, approximately 4 mm lateral to the limbus to implant the device through the pars plana. A device was removed from its package, rinsed with sterile saline, and examined for gross defects. Using a jewler's forceps, the device was grasped by the tether loop and inserted through the incision into the vitreous. After placement, the sclera was closed with interrupted 8-0 nylon sutures which passed through the loop at the external end of the device. The conjunctiva was closed with interrupted 8-0 nylon as well. The speculum and drapes were removed, and the animal repositioned so the above procedure could be repeated on the contralateral eye.

On the day of surgery, the dogs (7 weeks old, weight approx. 10 lb.) were monitored for heart and respiratory rates, rectal temperature, blood pressure and general body condition. Each animal was identified with a unique number which was noted on the animal. Cyclosporin A (Sandoz, 100 mg/ml, 10 mg/kg) was given once daily (oral), starting one day prior to implantation. Prednisone (5 mg/kg) and Clavamox (15 mg/kg) were given twice daily (oral), starting at day of implantation. The animals were placed on appropriate feed and water ad libitum and were housed indoors with a dark/light cycle consistent with Eastern Standard Time. Room Temperature was maintained at 18–29° C. (65–84° F.). Humidity range was maintained at 30–70%.

All animals were monitored daily following the surgical procedure for signs of surgically-related complications. Animals were monitored on a weekly basis for the presence of the following: coughing, signs of weight loss, fever, aphthous stomatitis, ocular inflammation or discharge, or gross motor deficiencies. Animals were weighed and temperatures taken at pre-implantation within 3 days of implant, and 7 days post-implantation. Blood pressures were also taken pre-implantation and within 1 week of sacrifice.

For the collection of blood samples, 30 ml of blood was drawn for immunology screening at (1) the time of implant and (2) at sacrifice. Ten ml was placed in a heparinized green top tube at room temperature for peripheral blood lymphocytes; 10 ml was placed in a red top tube, without anticoagulants, on ice for serum; and 10 ml was submitted for a blood chemistry profile.

At the conclusion of the experiment, the animals were euthanized with an overdose of pentobarbital 360 mg/kg IV after initial sedation with ketamine and pentothal. The devices were surgically explanted, assayed for CNTF release, and then placed in 4% paraformaldehyde for histology submission. The eyes were enucleated and fixed in 50 cc Bouin's solution at room temperature for 8–12 hr. The eyes were then rinsed in water and stored in 70% EtOH, and submitted for histological examination. For histological analysis, 3 slides of paraffin embedded eyes, sectioned through optic nerve, dorsal-lateral, stained with hematoxylin and eosin (H&E), were ordered for each eye. The devices were fixed in 4% Para formaldehyde for 30 min to 2 hr and processed for paraffin or glycidylmethacrylate (GMA) embedding, sectioned, and stained for histological evaluation. Each device was reviewed to determine cell density and cell viability.

The CNTF output of devices was evaluated after explantation. Briefly, devices were incubated in Ultraculture (0. 5 ml/well) for 24 hr. which was then assayed for CNTF output. The average device output of CNTF was 1.62±0.4 ng/device/24 hr. (This is one example of a "therapeutically effective" amount.) The individual device output is presented in TABLE 8.

TABLE 8

CNTF OUTPUT FROM EXPLANTED DEVICES

| Device # | CNTF (ng/Device/24 hr) |
| --- | --- |
| 1 | 1.65 |
| 2 | 1.9 |
| 3 | 2.45 |
| 4 | 1.1 |
| 5 | 1.4 |
| 6 | 1.3 |
| 7 | 1.7 |
| 8 | 1.62 |
| Mean ± SD | 1.62 ± 0.4 |

Encapsulated ARPE-P544 cells protected photoreceptors in the mutant dog model for retinal degeneration. Protection was defined by the degree of photoreceptor sparing. The non-affected dogs had 10–12 layers of ONL, while affected, non-treated dogs had 2–3 layers of ONL. The affected CNTF treated dogs had 5–6 layers of ONL. The results are presented in TABLE 9.

TABLE 9

NUMBER OF NUCLEI IN THE OUTER NUCLEAR LAYER (ONL) IN CNTF TREATED/UNTREATED rcd1 AND NON-AFFECTED DOGS ACROSS 6 AREAS OF THE RETINA

| Dog#, Eye | Superior Retina[c] | | | Inferior Retina[d] | | |
| --- | --- | --- | --- | --- | --- | --- |
|  | S1 | S2 | S3 | I1 | I2 | I3 |
| 1485L[a] | 4–6 | 6 | 6 | 4 | 4 | 4 |
| 1485R[a] | 3–4 | 3 | 4 | 2–3 | 2–3 | 2–3 |
| 1489L[a] | 5–6 | 7–8 | 7–8 | 5–6 | 4–5 | 5 |
| 1489R[a] | 3–4 | 3–4 | 3–4 | 3–4 | 4–5 | 2–3 |

TABLE 9-continued

NUMBER OF NUCLEI IN THE OUTER NUCLEAR LAYER (ONL) IN CNTF TREATED/UNTREATED rcd1 AND NON-AFFECTED DOGS ACROSS 6 AREAS OF THE RETINA

| Dog#, Eye | Superior Retina[c] | | | Inferior Retina[d] | | |
|---|---|---|---|---|---|---|
|  | S1 | S2 | S3 | I1 | I2 | I3 |
| 1487L[b] | 10–11 | 11–12 | 9–10 | 11–12 | 10–11 | 8 |
| 1487R[b] | 11–12 | 10–11 | 9 | 11–12 | 10 | 9 |

[a]. affected rcd1 dog
[b]. non-affected dog
[c]. Superior Retina = 7–8 10x fields long; 18 40x fields  S1 = 2 10x fields peripheral from optic nerve (4-40x fields peripheral)  S2 = midpoint between optic nerve & ora serrata  S3 = 2 10x fields central from ora serrata (4–40x fields central)
[d]. Inferior Retina = 5–6 10x fields long; 10 40x fields  I1 = 1 10x fields peripheral from optic nerve (3 4x fields peripheral)  I2 = midpoint between optic nerve & ora serrata  I3 = 1 10x fields central from ora serrata (3 40x fields central)

Histological evaluation indicated that all devices contain healthy viable cells. No cellular necrosis was observed in any of the devices. No immune reaction, inflammation or damage to the retina was observed.

7. ARPE-19 triggers low level host immune reaction.

(a) HLA class I and class II-DR. Baseline studies on cell lines Hs27 and ARPE-19 were carried out to determine the resting expression levels of the human HLA class I and HLA class II-DR molecules. The major histocompatibility marker W6/32 is normally expressed on any nucleated cell. In contrast, the HLA-class II DR marker is expressed on a more specific population of cells. Normally, the HLA class II DR molecule is found on B lymphocytes, monocytes, activated T cells, activated natural killer (NK) cells, and human progenitor cells.

TABLE 10 summarizes the non activated levels of expression from staining using the flow cytometer.

TABLE 10

CELL SCREENING FLOW CYTOMETRY (% POSITIVE)

| Cell | HLA Class I Monoclonal W6/32 IgG 2a | HLA Class II DR Becton Dickinson clone L243 IgG 2a |
|---|---|---|
| Hs27 P9 human skin fibroblast | 80.1 | 3.1 |
| ARPE P37 | 98.1 | 3.2 |
| Cyno B083 110492 positive control | 98.7 | 23.1 |
| BHK NGF P47 negative control | 0.1 | 0.03 |

(b) Allogeneic vs. xenogeneic antibody responses. Serum samples from either dog hosts or human hosts were evaluated using ARPE-19, Hs27 (human derived) and SIRC (rabbit derived) as target cells. To evaluate the specific anti-ARPE-19 IgG titer, ARPE-19 cells were used as target cells for flow cytometric analysis. ARPE-19 cells (100,000 cells/100 µl) were incubated with 25 µl of host serum, serially diluted up to a titer of 4×10⁶ and were then tagged with a fluorescein isothiocyanate (FITC) labeled second antibody (ICN Pharmaceuticals, Costa Mesa, Calif., USA). Data acquisition and histogram analysis was performed using a Becton Dickinson FACSort™(Becton Dickinson Immunocytometry Systems, San Jose, Calif., USA) with a 488 nm excitation and a single air cooled argon laser. Data were interpreted using CELLQuest™(Becton Dickinson Immunocytometry Systems, San Jose, Calif., USA) software with a 256 channel program and geometric/channel preferences.

Figure 2:
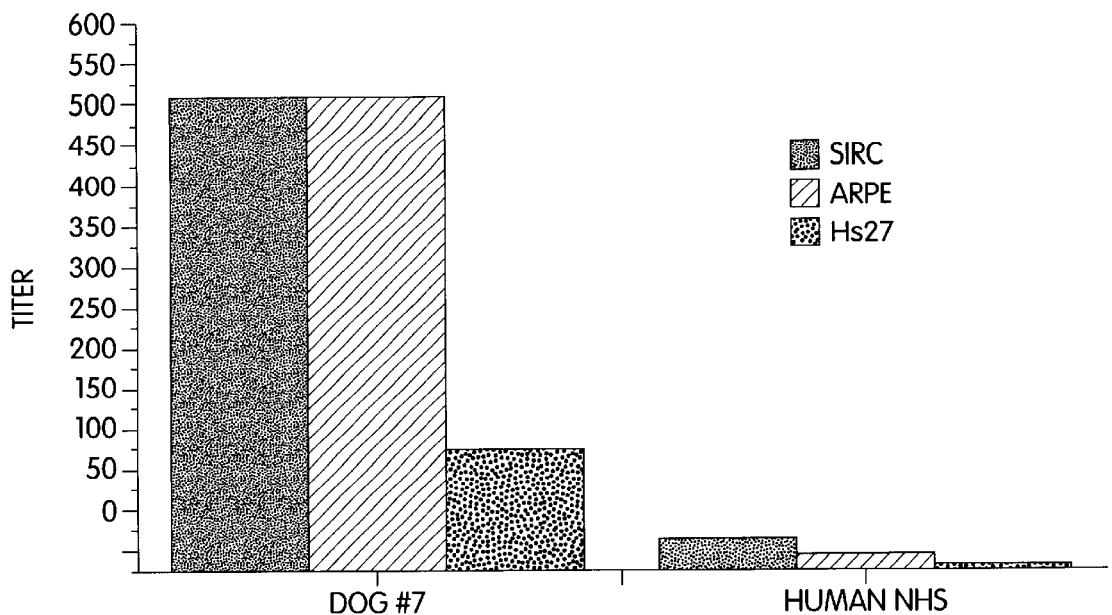
FIG. 2 is a bar graph showing anti-ARPE-19 specific IgG titer in dog vs. human serum. ARPE-19, Hs27, and SIRC cells were incubated with either dog or human serum dilutions. The antibody titer was measured by flow cytometric crossmatch (FCXM).

All data were reported as an increase in mean channel shift fluorescence (MCS) over the negative control samples. A shift of greater than 10 channels was considered positive. The results show that dog serum contains antibodies at much higher titer compared to human serum (FIG. 2).

Allogeneic vs. xenogeneic complement dependent cytotoxicity (CDC) responses. To determine the titer of cytotoxic antibodies specific to ARPE-19 cells, ARPE-19 cells were used as target cells in a complement-dependent cytotoxicity assay. The complement fixation of cytotoxic antibody titer was evaluated using either dog serum or human serum samples. ARPE-19, Hs27 and SIRC cells were used as the targets. All serum samples were set up in two groups of triplicates and assayed employing a standard National Institutes of Health (NIH) tissue typing technique (American Society for Histocompatibility and Immunogenetics (ASHI) Manual, 1994). One group of triplicates was analyzed with 1 µl of host serum and ARPE-19 cells (1000 cells/1 µl); the second group of triplicates was assayed in the same manner with the addition of 5 µl exogenous prescreened rabbit complement (Pel Freez Brown Deer, Wis., USA). Samples were prepared using a two-color immunofluorescent microcytotoxic analysis procedure. A 1 hr room temperature incubation of host serum and ARPE-19 cells was followed by a second 1 hr room temperature incubation with or without additional rabbit complement. In the same microtiter well, the percentage of living cells (negative reactivity) was visualized using fluorescein diacetate, while the percentage of dead cells (positive reactivity) was visualized using propidium iodide. All serum specimens were set up in 1:2 serial dilutions to a maximum of a 1:100,000 dilution. All data was scored using a Nikon Diaphot™ inverted fluorescence microscope with a 488 nm wavelength excitation.

Figure 3:
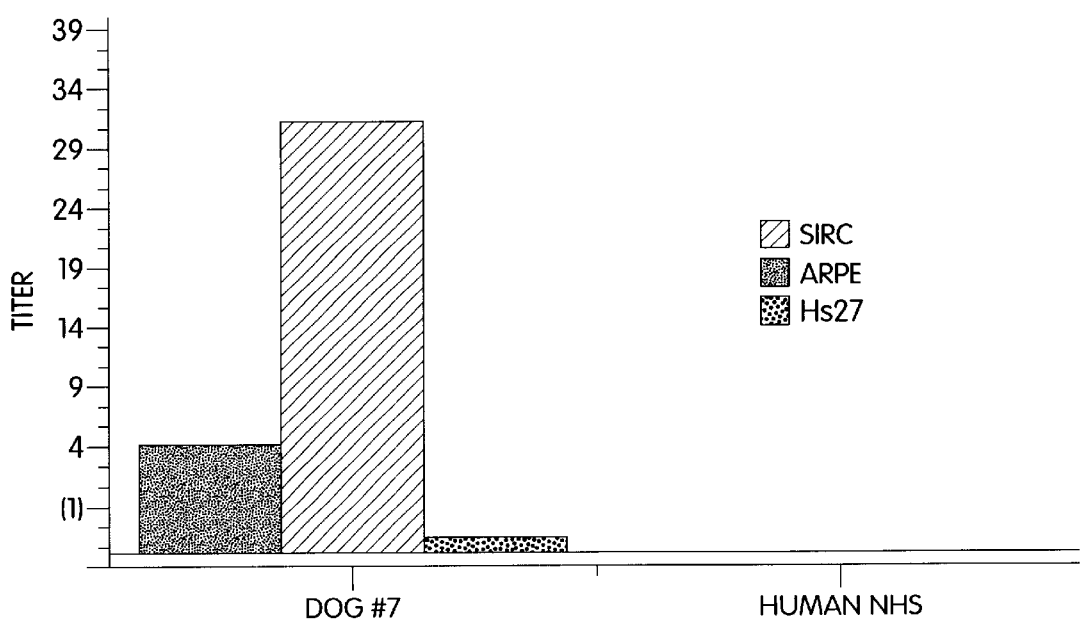
FIG. 3 is a bar graph showing cytotoxic ARPE-19 specific antibody titer in dog vs. human serum. ARPE-19, Hs27, and SIRC cells were incubated with either dog or human serum dilutions. The cytotoxic antibody titer was measured by complement dependent cytotoxicity crossmatch (CDC).

The results show that dog serum contained antibodies which can activate complement in the presence of these cells. In contrast, human serum did not fix the complement (FIG. 3).

8. The ARPE-19 cell line is nontumorigenic.

A tumorigenicity study of ARPE-19 cells was conducted following the procedure required by the U.S. Food and Drug Administration (FDA), Points to consider in the characterization of cell lines used in the productions of biologicals, 58 Federal Register 42974 (Aug. 12, 1993). Briefly, 10 million cells in 0.2 ml of serum free medium (PBS+10 mM.glucose) were injected subcutaneously into each nude mouse (irradiated Swiss nude mice, 2–7 days after irradiation, n=10). The animals were observed daily for 3 weeks for the evidence of tumor formation. At that time, half the animals were sacrificed, dissected and histologically examined to ensure the presence of the cells. The remaining animals were observed for an additional 12 weeks. The ARPE-19 cells showed no tumor formation in the nude mice for the 15-week study period.

B. Cell Encapsulation Methods and Devices

Encapsulated cell therapy is based on the concept of isolating cells from the recipient host's immune system by surrounding the cells with a semipermeable biocompatible material before implantation within the host. The invention includes a device in which ARPE-19 cells are encapsulated in an immunoisolatory capsule. An "immunoisolatory capsule" means that the capsule, upon implantation into a recipient host, minimizes the deleterious effects of the host's immune system on the ARPE-19 cells in the core of the device. ARPE-19 cells are immunoisolated from the host by enclosing them within implantable polymeric capsules formed by a microporous membrane. This approach prevents the cell-to cell contact between host and implanted tissues, eliminating antigen recognition through direct presentation. The membranes used can also be tailored to control the diffusion of molecules, such as antibody and complement, based on their molecular weight (Lysaght et al., 56 J. Cell Biochem. 196 (1996), Colton, 14 Trends Biotechnol. 158 (1996)). Using encapsulation techniques, ARPE-19 cells can be transplanted into a host without immune rejection, either with or without use of immunosuppressive drugs. Useful biocompatible polymer capsules usually contain a core that contains cells, either suspended in a liquid medium or immobilized within an immobilizing matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated ARPE-19 cells from immune destruction. The semipermeable nature of the capsule membrane also permits the biologically active molecule of interest to easily diffuse from the capsule into the surrounding host tissue.

The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by PCT International patent applications WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the transformed cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation (U.S. Pat. No. 5,512,600, incorporated by reference). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (PCT International patent application Ser. No. 98/05304, incorporated by reference). Woven mesh tubes have been used as vascular grafts (PCT International patent application WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly (acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. No. 4,976,859 or U.S. Pat. No. 4,968,733, incorporated by reference. An alternate surrounding semipermeable membrane material is poly(acrylonitrile/covinyl chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

When macrocapsules are used, preferably between $10^3$ and $10^8$ ARPE-19 cells are encapsulated, most preferably $10^5$ to $10^7$ ARPE-19 cells are encapsulated in each device. Dosage may be controlled by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of ARPE-19 cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see, PCT International patent application WO 97/34586, incorporated by reference).

C. Genetic Engineering of ARPE-19 Cells

As described above, ARPE-19 cells can be genetically engineered. The terms "genetic modification" and "genetic engineering" refer to the stable or transient alteration of the genotype of an APRE-19 cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

Any useful genetic modification of the APRE-19 cells is within the scope of the invention. For example, APRE-19 cells may be modified to produce or increase production of a biologically active substance such as a neurotransmitter or growth factor or the like. The genetic modification can be performed either by infection with viral vectors (retrovirus, modified herpes viral, herpes-viral, adenovirus, adeno-associated virus, and the like) or transfection using methods known in the art (lipofection, calcium phosphate transfection, DEAE-dextran, electroporation, and the like) (see, Maniatis et al., in *Molecular Cloning: A Laboratory Manual* (Cold Spring Harbor Laboratory, N.Y., 1982)). For example, the chimeric gene constructs can contain viral, for example retroviral long terminal repeat (LTR), simian virus 40 (SV40), cytomegalovirus (CMV); or mammalian cell-specific promoters. In addition, the vectors can include a drug selection marker, such as the *E. coli* aminoglycoside phosphotransferase gene, which when co-infected with the test gene, confers resistance to geneticin (G418), a protein synthesis inhibitor.

APRE-19 cells can be genetically modified using transfection with expression vectors. An "expression vector" is a nucleic acid either integrated in the genome or present in the cytoplasm, and capable of permitting the expression of the polypeptide, protein or viral vector. In one protocol, vector DNA containing the genes are diluted in 0.1×TE (1 mM Tris pH 8.0, 0.1 mM EDTA) to a concentration of 40 µg/ml. 22 µl of the DNA is added to 250 µl of 2×HBS (280 mM NaCl, 10 mM KCl, 1.5 mM $Na_2HPO_4$, 12 mM dextrose, 50 mM HEPES) in a disposable, sterile 5 ml plastic tube. 31 µl of 2 M $CaCl_2$ is added slowly and the mixture is incubated for 30 minutes (min) at room temperature. During this 30 min incubation, the cells are centrifuged at 800 g for 5 min at 4° C. The cells are resuspended in 20 volumes of ice-cold PBS and divided into aliquots of $1 \times 10^7$ cells, which are again centrifuged. Each aliquot of cells is resuspended in 1 ml of the DNA-$CaCl_2$ suspension, and incubated for 20 min at room temperature. The cells are then diluted in growth medium and incubated for 6–24 hr at 37° C. in 5%–7% $CO_2$. The cells are again centrifuged, washed in PBS and returned to 10 ml of growth medium for 48 hr.

Suitable vehicles for direct DNA, plasmid polynucleotide, or recombinant vector administration include, without limitation, saline, or sucrose, protamine, polybrene, polylysine, polycations, proteins, calcium phosphate, or spermidine. See e.g, PCT International patent application WO 94/01139.

APRE-19 cells can also be genetically modified using calcium phosphate transfection techniques. For standard calcium phosphate transfection, the cells are mechanically dissociated into a single cell suspension and plated on tissue culture-treated dishes at 50% confluence (50,000–75,000 cells/$cm^2$) and allowed to attach overnight. In one protocol, the modified calcium phosphate transfection procedure is performed as follows: DNA (15–25 µg) in sterile TE buffer (10 mM Tris, 0.25 mM EDTA, pH 7.5) diluted to 440 µλ with TE, and 60 µl of 2 M $CaCl_2$ (pH to 5.8 with 1M HEPES buffer) is added to the DNA/TE buffer. A total of 500 µl of 2×HeBS (HEPES-Buffered saline; 275 mM NaCl, 10 mM KCl, 1.4 mM $Na_2$ $HPO_4$, mM dextrose, 40 mM HEPES buffer powder, pH 6.92) is added dropwise to this mix. The mixture is allowed to stand at room temperature for 20 min. The cells are washed briefly with 1×HeBS and 1 ml of the calcium phosphate precipitated DNA solution is added to each plate, and the cells are incubated at 37° C. for 20 min. Following this incubation, 10 ml of "Complete Medium" is added to the cells, and the plates are placed in an incubator (37° C., 9.5% $CO_2$) for an additional 3–6 hours. The DNA and the medium are removed by aspiration at the end of the incubation period. The cells are washed, fresh medium is added and then cells are returned to the incubator.

Alternatively, the calcium phosphate co-precipitation technique can be used, as described in PCT International patent application WO 93/06222.

Moreover, ARPE-19 cells can be genetically engineered to produce a desired secreted factor. The desired secreted factor can be encoded by either a synthetic or recombinant polynucleotide. The term "recombinant" refers to the molecular biological technology for combining polynucleotides to produce useful biological products, and to the polynucleotides and peptides produced by this technology. The polynucleotide can be a recombinant construct (such as a vector or plasmid) which contains the polynucleotide encoding the desired secreted factor under the operative control of polynucleotides encoding regulatory elements such as promoters, termination signals, and the like. "Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence which is transcribed and translated into a polypeptide. Two coding polynucleotides are "operably linked" if the linkage results in a continuously translatable sequence without alteration or interruption of the triplet reading frame. A polynucleotide is operably linked to a gene expression element if the linkage results in the proper function of that gene expression element to result in expression of the desired secreted factor. "Transformation" is the insertion of an exogenous polynucleotide (i.e., a "transgene") into a host cell. The exogenous polynucleotide is integrated within the host genome. A polynucleotide is "capable of expressing" a desired secreted factor if it contains nucleotide sequences which contain transcriptional and translational regulatory information and such sequences are "operably linked" to polynucleotide which encode the desired secreted factor. A polynucleotide that encodes a peptide coding region can be then amplified, for example, by preparation in a bacterial vector, according to conventional methods, for example, described in the standard work Sambrook et al., *Molecular Cloning: A Laboratory Manual* (Cold Spring Harbor Press 1989). Expression vehicles include plasmids or other vectors.

The polynucleotide encoding the desired secreted factor can be prepared by chemical synthesis methods or by recombinant techniques. The polypeptides can be prepared conventionally by chemical synthesis techniques, such as described by Merrifield, 85 J. Amer. Chem. Soc. 2149–2154 (1963) (see, Stemmer et al, 164 Gene 49 (1995)). Synthetic genes, the in vitro or in vivo transcription and translation of which will result in the production of the desired secreted factor protein can be constructed by techniques well known in the art (see Brown et al., 68 Methods in Enzymology 109–151 (1979)). The coding polynucleotide can be generated using conventional DNA synthesizing apparatus such as the Applied Biosystems Model 380A or 380B DNA synthesizers (commercially available from Applied Biosystems, Inc., 850 Lincoln Center Drive, Foster City, Calif., USA).

Polynucleotide gene expression elements useful for the expression of cDNA encoding desired secreted factor include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Recipient cells capable of expressing the desired secreted factor are then transfected. The transfected recipient cells are cultured under conditions that permit expression of the desired secreted factor, which is recovered from the culture. ARPE-19 cells can be used in connection with poxvirus vectors, such as vaccinia or swinepox. Suitable non-pathogenic viruses which can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething & Sambrook, 293 Nature 620–625 (1981)). Another preferred system includes the baculovirus expression system and vectors.

The polynucleotide encoding the desired secreted factor can be used in a variety of ways. For example, a polynucleotide can express the desired secreted factor peptide in vitro in a host cell culture. The expressed desired secreted factor, after suitable purification, can then be incorporated into a pharmaceutical reagent or vaccine (described below).

Determinations of the sequences for the polynucleotide coding region that codes for the desired secreted factor described herein can be performed using commercially available computer programs, such as DNA Strider and Wisconsin GCG. Owing to the natural degeneracy of the genetic code, the skilled artisan will recognize that a sizable yet definite number of DNA sequences can be constructed which encode the claimed peptides (see, Watson et al., *Molecular Biology of the Gene,* 436–437 (the Benjamin/ Cummings Publishing Co. 1987)).

The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are "neurological agents", a term which encompasses any biologically or pharmaceutically active substance that may prove potentially useful for the proliferation, differentiation or functioning of CNS or eye cells or treatment of neurological or opthalmological disease or disorder. For example, the term may encompass certain neurotransmitters, neurotransmitter receptors, growth factors, growth factor receptors, and the like, as well as enzymes used in the synthesis of these agents.

When the genetic modification is for the production of a biological agent, the substance can be one that is useful for the treatment of a given CNS or eye disorder. APRE-19 cells can be genetically modified to express a biologically active agent, such as growth factors, growth factor receptors, neurotransmitters, neurotransmitter synthesizing genes, neuropeptides, and chromaffin granule amine transporter. For example, it may be desired to genetically modify cells so they secrete a proliferation-inducing growth factor or a differentiation-inducing growth factor.

The biological agent can be basic fibroblast growth factor (bFGF), acid fibroblast growth factor, epidermal growth factor, transforming growth factor $\alpha$, transforming growth factor $\beta$, nerve growth factor, insulin like growth factor, platelet derived growth factor, glia-derived neurotrophic factor, brain derived neurotrophic factor, ciliary neurotrophic factor, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor $\alpha$, fibroblast growth factor receptor, epidermal growth factor receptor, or other agents expected to have therapeutically useful effects on potential target tissues. Examples of biological agents include trophic factors such as glial-derived neurotrophic factor (GDNF); regulators of intracellular pathways associated with growth factor activity such as staurosporine, CGP-4 1251, and the like; hormones; various proteins and polypeptides such as interleukins; oligonucleotides such as antisense strands directed, for example, against transcripts for receptors; heparin-like molecules; and a variety of other molecules that have an effect on radial glial cells or CNS neural stem cell.

ARPE-19 cells that secrete IL-2 can be created by transfection of ARPE-19 with with the plasmid vector pBCMG-hygro-hIL-2 (Roux et al., 159 J. Cell. Physiol. 101–113 (1994)), an episomal expression vector containing the human IL-2 cDNA sequence under the transcriptional control of a cytomegalovirus (CMV) promoter including a rabbit $\beta$-globin intron, followed by a poly(A) sequence, and a hygromycin-resistant gene for selection. To introduce an expression vector encoding the hIL-2 protein into the ARPE-19 cell line, the calcium phosphate precipitation technique can be used. The pPCHIL plasmid (pBCMG-hIL-2) contains the hIL-2 cDNA sequence followed by the Hygromycin B resistance gene for selection. Cells which have stably integrated foreign DNA into their genome are selected in presence of Hygromycin B in the medium.

ARPE-19 cells that secrete IL-10 can be created. Interleukin-10 (IL-10), produced by the Th, subset of $CD_4$ cells, suppresses cytokine production by the $Th_1$, subset of CD4+ helper T-lymphocytes. IL-10 also inhibits the production of numerous pro-inflammatory cytokines by monocytes. IL-10 expression has been detected in human malignant gliomas and at higher levels in malignant vs. low grade tumors. This has led to the hypothesis that endogenous IL-10 functions to suppress anti-glioma immunity within brain. Despite the potentially immunosuppressive and anti-inflammatory actions of endogenous IL-10, evidence is mounting that transgenic IL-10produced at high levels by engineered tumor cells can inhibit growth of systemic tumors by either stimulating anti-tumor immunity or inhibiting tumor-associated angiogenesis. IL-10-producing ARPE-19 cells can be created by transfection with the plasmid pBMGneo. IL-10 in the presence of lipofectamine (GIBCO) using a procedure similar to that of Kundu et al., 88 J. Natl. Cancer Inst. 536–41 (1996).

ARPE-19 cells that secrete FGF can be created. Fibroblast growth factor (FGF) is an endothelial cell mitogen that can be neuroprotective for other cell types within the central nervous system. The ARPE-19 cell line can be genetically altered to express a chimeric human FGF-1 gene consisting of the hst/KS3 signal sequence of FGF-4 fused in-frame to FGF-1 (sp-hst/KS3:FGF-1) (Forough et al., 268 J. Biol. Chem. 2960–8 (1993)).

APRE-19 cells can be engineered to produce various neurotransmitters or their receptors such as serotonin, L-dopa, dopamine, norepinephrine, epinephrine, tachykinin, substance P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptides, which may prove useful in the treatment of CNS disorders, include substance-P, neuropeptide-Y, enkephalin, vasopressin, VIP, glucagon, bombesin, CCK, somatostatin, calcitonin gene-related peptide, and the like.

Alternatively, ARPE-19 cells can be constructed to produce retroviral gene transfer vectors using the methods of U.S. Pat. No. 5,614,404, describing recombinant viral vectors which coexpress heterologous polypeptides capable of assembling into defective nonself-propagating viral particles. Viruses useful as gene transfer vectors include retrovirus, which are the vectors most commonly used in human clinical trials. To generate a gene therapy vector, the gene of interest is cloned into a replication-defective retroviral plasmid which contains two long terminal repeats (LTR), a primer binding site, a packaging signal, and a polypurine tract essential to reverse transcription and the integration functions of retrovirus after infection. To produce viral vector, the plasmid form of a vector is transfected into a packaging cell line which produces Gag, Pol and Env of the retroviral structural proteins required for particle assembly. A producer cell line is usually generated using a selective marker, often a G418 resistant gene carried by the retroviral vector. The resulting cell line can be encapsulated, as described in PCT International patent application WO 97/44065, which describes biocompatible capsules containing living packaging cells that secrete a viral vector for infection of a target cell, and methods of delivery for an advantageous infectivity of the target cells.

The effects of the biological agents on cells of the CNS or eye in the recipient host can be identified in vitro based upon significant differences between model cell cultures for central nervous system cells (such as rat pheochromocytomaPC12 cells, cultured primary central nervous neurons, etc.); or eye cells (such as the IO/LD7/4 cell line, ARPE-19 cells, cultured retinal pigment epithelial cells, etc.) relative to control cultures with respect to criteria such as the ratios of expressed phenotypes (neurons, glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which synthesize these molecules. Also, the cellular detection of transcripts of the desired secreted factor in vivo can be demonstrated by immunochemistry or by other immunological methods.

D. Therapeutic Usefulness of Polymer Encapsulated ARPE-9 Cell Delivery of Growth factors The central nervous system is site that is subject to chronic degeneration. Growth factors are known to have a tremendous therapeutic potential for treating neurodegenerative disorders. For example, polymer-encapsulated xenogeneic cells that have been genetically engineered to secrete growth factors can protect against lesion-induced cell loss in the central nervous system in rats (Winn et al., 91 Proc. Natl. Acad. Sci. USA 2324–8 (1994)), primates (Emerich et al., 349 J. Comp. Neurol. 148–64 (1994)), and aged primates (Kordower et al., 91 Proc. Natl. Acad. Sci. USA 10898–902 (1994)). Therapeutic effects have been produced with polymer-encapsulated cell devices directly delivering various growth factors to a range of target sites in the central nervous system with no evidence of adverse effects (Emerich et al., 130 Exp. Neurol. 141–50 (1994), Emerich et al, 736 Brain Res. 99–110 (1996), Emerich et al., 349 J. Comp. Neurol. 148–64 (1994), Hoffman et al., 122 Exp. Neurol. 100–6 (1993), Kordower et al., 72 Neuroscience 63–77 (1996), Kordower et al., 91 Proc. Natl. Acad. Sci. USA 10898–902 (1994), Winn et al., 91 Proc. Natl. Acad. Sci. USA 2324–8 (1994)). The safety of polymer-encapsulated cell delivery of growth factors is supported by studies that found no adverse effects in animals receiving growth factors delivered to the brain for up to one year (Lindner et al., 5 Cell Transplant. 205–23 (1996), Winn et al., 140 Exp. Neurol. 126–38 (1996)). These studies found no adverse effects even in tests of learned behaviors, which are extremely sensitive to neurotoxicity.

The retina is another site subject to chronic degeneration. Development of treatments for retinal degeneration is also complicated by problems of drug delivery to the posterior chamber of the eye. Recently, several studies have shown that ciliary neurotrophic factor (CNTF) can be therapeutic for ophthalmic disorders. CNTF has been shown to protect the retina from ischemic injury (Unoki & LaVail, 35 Invest. Ophthalmol. Vis. Sci. 907–15 (1994)). LaVail et al. (89 Proc. Natl. Acad. Sci. USA 11249–53 (1992); and 39 Invest. Ophthalmol. Vis. Sci. 592–602 (1998)) reported that CNTF exhibited more therapeutic potential than 8 other growth factors with respect to the ability of growth factors to protect retinal photoreceptors in rat eyes exposed to light-induced degeneration. Cayouette et al. (18 J. Neurosci. 9282–93 (1998), Cayouette & Gravel, 8 Hum. Gene Ther. 423–30 (1997)) has shown that chronic CNTF delivery produces a lasting cell sparing and improves the function of surviving photoreceptors in mouse models of retinitis pigmentosa.

Age-related macular degeneration (AMD) is the leading cause of irreversible visual loss in the USA. Age-related macular degeneration is the most common geriatric eye disorder leading to blindness and is characterized by degeneration of the neuroepithelium in the macular area of the eye. Apolipoprotein E (apoE) appears to be associated with neurodegeneration. The dry form of the disease is more common than the wet, but the wet form causes the most severe vision loss. Other than vision aids (e.g., glasses, magnifiers), no treatments or preventive measures are currently available for patients with dry macular degeneration, and laser photocoagulation with fluorescein angiography is the only clinically proven therapy for neovascular disease (see, Starr et al., 103(5) Postgrad Med. 153–6, 161–4 (1998)). Laser photocoagulation of choroidal neovascular membranes (CNVMs) in exudative AMD has previously been the only well-studied and widely accepted treatment modality. This treatment is beneficial for only a small minority of patients who show well-demarcated "classic" CNVMs.

Retinitis pigmentosa (RP) is a genetic disorder that causes the degeneration of cells in the retina. If severe, it may lead to complete blindness.

Diabetic eye disease refers to a group of sight-threatening eye problems that people with diabetes may develop as a complication of the disease. They include diabetic retinopathy, which damages blood vessels in the retina, the light-sensitive tissue at the back of the eye that translates light into electrical impulses that the brain interprets as vision. Diabetic retinopathy affects about half of the Nation's estimated 16 million people with diabetes have at least early signs of diabetic retinopathy. Of this group, about 700,000 have serious retinal disease, with approximately 65,000 Americans progressionally each year to proliferative retinopathy, the disease's most sight-threatening stage. Annually as many as 25,000 people go blind from the disorder, making it a leading cause of blindness among working-age Americans.

The cost of diabetic retinopathy is high, as a year of blindness costs the U.S. Government approximately $13,607 annually per person in Social Security benefits, 1 income tax revenue, and health care expenditures.

Because growth factors are known to be useful in treating neurological or retina degeneration, and because encapsulated ARPE-19 cells can be genetically engineered to secrete growth factors, the invention provides a method for treating neurological or retina degeneration.

E. Conclusion

The ARPE-19 cell line is surprisingly useful for the cell-based delivery of factors to a recipient host. For example:

(a) The ARPE-19 cell line is a platform cell line for cellular therapy.
(b) Transplantation of ARPE-19 cells is useful for administering a desired therapy factor for treating neurodegenerative diseases.
(c) The ARPE-19 cell line is a platform cell line for cellular therapy whenin the ARPE-19 cells are unencapsulated.
(d) The ARPE-19 cell line is a platform cell line for cellular therapy wherein the ARPE-19 cells are encapsulated.
(e) The ARPE-19 cell line is a platform cell line for cellular therapy wherein the ARPE-19 cells the cells are genetically modified to secrete a desired therapeutic factor.
(f) The ARPE-19 cell line is a platform cell line for cellular therapy wherein the ARPE-19 cells are genetically modified to secrete a desired therapeutic protein when the desired proteins include (but are not limited to) neurotrophins, interleukins, cytokines, anti-apoptotic, angiogenic, and anti-angiogenic factors, and antigens. Such factors also include brain derived neurotrophic factor (BDNF), neurotrophin-4 (NT-4), CNTF, Axokine (second generation ciliary neurotrophic factor (CNTF); RegeneronPharmaceuticals Inc.), basic fibroblast growth factor (bFGF), the insulin like growth factors IGF I and IGF II, TGFβ II, the heparin-binding cytokine Midkine (MK), interleukin 1 (IL-1β), tumor necrosis factor (TNF), nerve growth factor (NGF), IL-2/3, ILF, IL-6, Neurturin (NTN), Neublastin, VEGF, glial cell line-derived neurotrophic factor (GDNF), platelet-derived growth factor (PDGF), lens epithelium-derived growth factor (LEDGF), and pigment epithelium-derived factor (PEDF).
(g) The ARPE-19 cell line is a platform cell line for cellular therapy wherein the ARPE-19 cells are implanted into a mammal, to administer a therapeutically effective amount of desired factor to the mammal.
(h) The ARPE-19 cell line is a platform cell line for cellular therapy wherein the ARPE-19 cells are implanted into the central nervous system, eye or any other tissue of interest.
(i) The ARPE-19 cell line is a platform cell line for cellular therapy wherein the ARPE-19 cells are implanted into the central nervous system, where the central nervous system sites include ventricular and intrathecal spaces, striatum, and other sites in the brain or spinal cord parenchyma.
(j) The ARPE-19 cell line is a platform cell line for cellular therapy wherein the ARPE-19 cells are implanted into the eye, where the eye sites include subretinal and intravitreal spaces.
(k) Transplantation of ARPE-19 cells is useful for administering a therapeutic protein for treating degenerative diseases, where the degenerative diseases include (but not limited to) Parkinson's Disease, Huntington's Disease, ALS, Alzheimer's Disease, Spinal Cord Injury, Retinopathy of Prematurity, Diabetic Retinopathy, Age-Related Macular Degeneration, Glaucoma, Retinitis Pigmentosa, Cataract Formation, Retinoblastoma, Retinal Ischemia.
(l) Transplantation of ARPE-19 cells is a method for administering a therapeutic protein for treating cancer and cancer related disorders, cardiovascular deseases, asthma, metabolic diseases and other relevant pathologies.
(m) Transplantation of ARPE-19 cells is a method for administering a desired antigenic factor as a vaccine.
(n) The ARPE-19 cell line can be a packaging cell line to produce viral gene transfer vectors.
(o) Transplantation of ARPE-19 cells is a method for delivering a desired factor to a recipient host. ARPE-19 cells, encapsulated within a semipermeable membrane that allows the diffusion of the growth factor; are implanted into a target region within the recipient host, such that the encapsulated ARPE-19 cell secretes the desired factor to the target region.

The deposited subject cultures discussed above are deposited under conditions that ensure that access to the cultures will be available during the pendency of the patent application disclosing them to one determined by the Commissioner of Patents and Trademarks to be entitled thereto under 37 C.F.R. §1.14 and 35 U.S.C. §122. The deposits are available as required by foreign patent laws in countries where counterparts of the subject application, or its progeny, are filed. However, the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least 30 years after the date of deposit or for the enforceable life of any patent which may issue disclosing the cultures plus 5 years after the last request for a sample from the deposit. The depositor acknowledges the duty to replace the deposits should the depository be unable to furnish a sample when requested, due to the conditions of the deposits. All restrictions on availability to the public of the subject culture deposits will be irrevocably removed upon granting of a patent disclosing them.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

We claim:

1. An implantable cell culture device, the device comprising:
    (a) a semipermeable membrane permitting the diffusion of a growth factor therethrough; and
    (b) ARPE-19 cells that are genetically engineered to produce the growth factor disposed within the semipermeable membrane.

2. The device of claim 1, wherein the semipermeable membrane is immunoisolatory.

3. The device of claim 1, wherein the semipermeable membrane is microporous.

4. The device of claim 1, wherein the semipermeable membrane permits the diffusion of a substance of therapeutic interest.

5. The device of claim 1, wherein the device further comprises a matrix disposed within the semipermeable membrane.

6. The device of claim 1, wherein the device further comprises a tether anchor.

7. The device of claim 1, wherein said growth factor is selected from the group consisting of brain derived neurotrophic factor (BDNF), neurotrophin-4 (NT-4), ciliary neurotrophic factor (CNTF), Axokine, bFGF, IGF I, IGF II, TGFβ II, Midkine, IL-1β, nerve growth factor (NGF), IL-2/3, IL-6, neurturin (NTN), Neublastin, VEGF, glial cell derived neurotrophic factor (GDNF), platelet derived growth factor (PDGF), lens epithelium derived growth factor (LEDGF), and pigment epithelium derived growth factor (PEDF).

8. The device of claim 7, wherein said growth factor is ciliary neurotrophic factor (CNTF).

9. The device of claim 7, wherein said growth factor is glial cell derived neurotrophic factor (GDNF).

10. A method for inhibiting retinal degradation, comprising implanting into the eye of a recipient host with retinal degeneration an implantable cell culture device, the device comprising:
    (a) a semipermeable membrane permitting the diffusion of a growth factor therethrough; and
    (b) ARPE-19 cells that are genetically engineered to secrete the growth factor;
    wherein the device releases a therapeutically effective amount of said growth factor into the eye of the host recipient, thereby inhibiting the retinal degradation.

11. The method of claim 10, wherein the growth factor is ciliary neurotrophic factor (CNTF).

12. The method of claim 11, wherein the therapeutically effective amount of CNTF is between 100–350 ng/million cells/24 hr (ng/M/d).

13. The method of claim 11, wherein the therapeutically effective amount of CNTF is about 1.62±0.4 ng/device/24 h.

14. The method of claim 10, wherein the retinal degradation is caused by a disorder selected from the group consisting of Retinophathy of Prematurity, Diabetic Retinophathy, Age-related Macular Degeneration, Glaucoma, Retinitis Pigmentosa, Cataract Formation, Retinoblastoma, and Retinal lschemia.

* * * * *